(12) United States Patent
Scott

(10) Patent No.: US 8,193,220 B1
(45) Date of Patent: Jun. 5, 2012

(54) METHOD OF CHANGING MUSCLE LENGTHS WITH ANESTHETIC DRUGS

(76) Inventor: Alan Brown Scott, Mill Valley, CA (US)

( * ) Notice: Subject to any disclaimer, the term of this patent is extended or adjusted under 35 U.S.C. 154(b) by 441 days.

(21) Appl. No.: 12/583,424

(22) Filed: Aug. 20, 2009

(51) Int. Cl.
*A61K 31/445* (2006.01)
(52) U.S. Cl. ....................................................... 514/330
(58) Field of Classification Search .................... 514/330
See application file for complete search history.

(56) References Cited

U.S. PATENT DOCUMENTS 5,841,622 A * 11/1998 McNulty, Jr. ................. 361/232
5,852,003 A * 12/1998 Barritault et al. ............... 514/54
6,233,484 B1 * 5/2001 Ben-Haim et al. ................ 607/9

* cited by examiner

*Primary Examiner* — Raymond Henley, III

(57) ABSTRACT

According to one aspect, the fibers of a muscle to be shortened or lengthened are exposed to a local anesthetic drug such as bupivacaine. The concentration and volume of the local anesthetic drug are sufficient to causes the muscle fibers to be damaged by the myotoxicity of the drug. The muscle is then kept at a different length, shorter or longer, during the ensuing period of muscle fiber regeneration, resulting in a shortened or lengthened muscle. In one embodiment, the shortened length of the treated muscle improved the position and the movement of the eye to which it was attached.

16 Claims, No Drawings

METHOD OF CHANGING MUSCLE LENGTHS WITH ANESTHETIC DRUGS

CROSS REFERENCE TO RELATED APPLICATION

This application is related to my pending application Ser. No. 11/867,532, filed Oct. 4, 2007, and titled "Medical Treatment Of Muscles By Exposure To Anesthetic Drugs."

BACKGROUND

Prior Art

Many medical conditions are the result of muscles that function improperly because they are too long or too short. One example is the controlling muscles of eyes. When the length of the controlling muscles is improper, the eyes become crossed or misaligned. Another example is that of the flexor muscles of an arm that is held in a flexed position after a stroke of the brain. Because such muscles lack proper brain control, they are over-active and become shortened, restricting movement. Yet another example is that of a child, who, as a result of cerebral palsy, has short and restricting muscles in the legs that limit limb movement and thereby interfere with walking. Yet another example is that of a muscle that is weakened by damage to its motor nerve, with consequent stretching and lengthening of the muscle by its intact antagonist muscles, so that, even if the nerve heals, the muscle is left too long to provide proper function.

Prior Methods of Lengthening and Shortening Muscles

Various methods of lengthening and shortening improperly functioning muscles exist. The following are some of these methods.

1. Physical therapy, exercise, and bracing to move the limb can be used to stretch shortened muscles attached to the limb. These methods are well-established approaches and are generally safe, but they are time-consuming, often extending over many weeks or months, and uncomfortable, as stretching the muscles activates pain receptors. The methods are not applicable to many muscles, such as those of the eye and the larynx, because these muscles are deep in the body, so that there is no way to manipulate them as can be done with weights, springs, braces, or the pull of gravity with muscles attached to the limbs or the torso of the body.

2. Surgical repositioning of a muscle's origin or insertion or shortening or lengthening of the muscle's tendon can improve the function of a muscle. While this is an important method of treatment, it is invasive, painful, carries risks as with all surgery, and requires hospitalization for all but the simplest procedures.

3. Botulinum toxin injection into a muscle blocks nerve transmission to the muscle. This can relax a shortened muscle, allowing it to be lengthened by exercise, by bracing, or by the pull of the antagonist muscle, as functional length units (sarcomeres) are added or removed from the muscle. (Scott A B. Change of eye muscle sarcomeres according to eye position. *J Pediatr Ophthalmol Strabismus*. 1994; 31 (2): 85-8.) The muscle tends to return to its former length, however, so that lasting length change is not reliably attained in eye muscles in treating strabismus or in leg muscles of children with motor cerebral palsy. Therefore, repeated injections are often required.

4. Electrical stimulation through electrodes applied to the skin over the muscle can activate and shorten muscles. This method is useful for limb muscles, but no embodiment of this approach can be used for small muscles such as those in the larynx or in the eye due to the depth of these muscles in the body.

To the best of my knowledge, the deficiencies of these prior methods for muscle lengthening and shortening have continued.

Prior Basic Science Work with Local Anesthetics and Muscles

Muscles are made up of many functional length units (sarcomeres) strung together like the links in a chain. It is known that within minutes after exposure to the local anesthetic drug bupivacaine, there is a dissolution of the connections between these sarcomere units, resulting in an irreversible breakdown of the muscle fibers. (Sokoll M D, Sonesson B, and Thesleff S. Denervation changes produced in an innervated skeletal muscle by long-continued treatment with a local anesthetic. *Euro J of Pharmacology*. 1968; 4 (2): 179-187)

Both the amino-amide and aceto-amide classes of local anesthetics have this toxic effect on muscle fibers. (Bradley W. Muscle fiber splitting. (pp. 215-232), In Muscle Regeneration. 1979 Raven Press, New York; Hall-Craggs E C. Rapid degeneration and regeneration of whole skeletal muscle following treatment with bupivacaine (Marcain). *Exp Neurol*. 1974; 43: 349-358; Hall-Craggs E C & Seyan H S. Histochemical changes in innervated and denervated skeletal muscle fibers following treatment with bupivacaine (Marcain). *Exp Neurol*. 1975; 46 (2): 345-354; Libelius R, Sonesson B, Stamenovic B A, and Thesleff S. Denervation-like changes in skeletal muscle after treatment with local anaesthetic (Marcaine). *J Anat*. 1970; 106 (2): 297-309)

Several investigators have suggested or studied the application of anesthetic drugs as a treatment to weaken overly active muscles. If a muscle can be weakened or its over-activity reduced by this method of damaging the muscle fibers, the condition would be improved. However, the muscle regenerates after this chemical damage from the anesthetic drugs, so that no lasting effect is achieved. (Park C M, Park S E, Oh S Y. Acute effects of bupivacaine and ricin mAb35 on extraocular muscle in the rabbit. *Curr. Eye Res*. 2004; 29: 293-301; McLoon L K, & Wirtschafter J. Regional differences in subacute response of rabbit orbicularis oculi to bupivacaine-induced myotoxicity as quantified with a neural cell adhesion molecule immunohistochemical marker. *IOVS* 1993; 34 (12): 3450-3458.)

The damaged muscle fibers are not repaired, but are removed by macrophage cells, and new replacement fibers are made by nearby satellite cells. (Benoit P W, & Belt W D. Destruction and regeneration of skeletal muscle after treatment with a local anaesthetic, bupivacaine (Marcaine). *J Anat*. 1970; 107 (Pt 3): 547-556; Carlson B M, Shepard B, and Komorowski T E. A histological study of local anesthetic-induced muscle degeneration and regeneration in the monkey. *J Orthop Res*. 1980; 8 (4): 485-494; Nonaka I, Takagi A, Ishiura, S, Nakase H & Sugita H. Pathophysiology of muscle fiber necrosis induced by bupivacaine hydrochloride (Marcaine). *Acta Neuropathol* (Berl.) 1983; 60 (3-4): 167-174.)

The basic cell membrane, the nerve supply, and the nearby satellite cells remain intact despite the damage to the muscle fibers inside the cell membrane. Within a few days, the satellite cells, a sort of stem cell that normally lies dormant within the muscle, begin to proliferate. They refill this framework with new muscle fibers over the next 7 to 21 days. (Hall-Craggs E C B. Survival of satellite cells following exposure to the local anesthetic bupivacaine (Marcaine). *Cell Tissue Res*. 1980; 209:131-135; Hall-Craggs E C B. Early ultrastructural changes in skeletal muscle exposed to the local anaesthetic bupivacaine (Marcaine). *Br J Exp Path* 1980; 61:139-149; Schultz E, Jaryszak D L. Effects of skeletal muscle regeneration on the proliferation potential of satellite cells. *Mech Ageing Devel.* 1985; 30: 63-72; McLoon L K, Nguyen L T, Wirtschafter J. Time course of the regenerative response in bupivacaine injured obicularis oculi muscle. *Cell Tissue Res.* 1998; 294:439-447)

Two papers have shown that bupivacaine injection into the extensor digitorum longus muscle in the hind limb of the rat is followed by enlargement of the muscle beyond its original size. These authors addressed muscle weight, strength, and stiffness in some degree, but did not address changes in muscle length as a consequence of exposure to the local anesthetic drug. (Rosenblatt J D. A time course study of the isometric contractile properties of rat extensor digitorum longus muscle injected with bupivacaine. *Comp Biochem Physiol.* 1992; 101 (2):361-367; Rosenblatt, J D, Woods R I. Hypertrophy of rat extensor digitorum longus muscle injected with bupivacaine; A sequential histochemical, immunohistochemical, histological, and morphometric study. *J. Anat.* 1992; 181:11-27. A third paper on this topic also discussed possible muscle lengthening by the addition of sarcomeres. This is the mechanism of lengthening described above in: Prior Methods of Lengthening and Shortening Muscles, item 3. Plant D R, Beitzel F, & Lynch G S. Length-tensionrelationships are altered in regenerating muscles of the rat after bupivacaine injection. *J Appl Physiol.* 2005; 98 (6):1998-2003).

Prior Clinical Work with Local Anesthetics and Muscles

Eye surgeons use the technique of injecting local anesthetic drugs into the orbit (eye socket) to block pain nerves and eye muscle nerves in preparation for cataract surgery. A misalignment (strabismus) of the injected eye is occasionally seen after the operation when the injection accidentally goes into one of the muscles that control the movement and position of the eye rather than into the orbital tissues. Clinical investigators consistently have attributed the altered movements of the injected eye to some form of scarring or fibrosis. (Rainin E A & Carlson B M. Postoperative diplopia and ptosis: A clinical hypothesis based on the myotoxicity of local anesthetics. *Arch Ophthalmol.* 1985; 103 (9):1337-1339; Grimmett M R & Lambert S R. Superior rectus muscle over-action after cataract extraction. *Am J. Opthalmol.* 1992; 114 (1):72-80; Munoz M. Inferior rectus muscle overaction after cataract extraction. *Am J Ophthalmol.* 1994; 118 (5): 664-6); Goldchmit M & Scott A B. Evaluation of ocular motility in patients injected with retrobulbar anesthesia. *Arq Bras Oftal.* 1994; 57:114-116: Hamed L M & Mancuso A. Inferior rectus muscle contracture syndrome after retrobulbar anesthesia *Ophthalmology.* 1991; 98:1506-1512: Capo H, Roth E, Johnson T, Munoz M & Siatkowski R M. Vertical strabismus after cataract surgery. *Ophthalmology.* 1996; 103(6): 918-921; Carlson B M, Emerick S, Komorowski T E, Rainin E A, & Shepard B M. Extraocular Muscle Regeneration in Primates. *Ophthalmology.* 1991; 99 (4):582-589)

The applicant has injected the local anesthetic bupivacaine into the eye muscles of patients to treat a misaligned eye (strabismus) The bupivacaine poisoned and damaged the injected muscles, resulting in a period of muscle weakness lasting from 7 to 16 days. The muscles regenerated during this period, followed by a 20-30 day period of hypertrophy (growth beyond the original state), with resulting correction or improvement of strabismus deviations by the enlarged stronger muscle. (Scott A B, Alexander D E, Miller J M. Bupivacaine injection of eye muscles to treat strabismus. *Br J. Ophthalmol.* 2007; 91 (2):146-148).

ADVANTAGES

One advantage of the present method is that muscles can be lengthened or shortened in a relatively short time, whereas physical therapy is often a continuous treatment over years.

Also, muscles of the eye, of the neck, and of the larynx, inaccessible to physical therapy, can be treated by aspects of the method.

The present method, in one or more aspects, has advantages over surgical treatment, as it employs a simple injection in the office, with no need for expensive hospitalization and extended recovery. The material injected is an anesthetic, so that pain is minimal, and there is no pain following injection. Recovery is complete in about a month after injection, whereas healing and rehabilitation after orthopedic muscle surgery often lasts several months.

The method has advantages over botulinum toxin injection in that the muscle exposed to local anesthetic drugs will recover useful action within 7-16 days and be fully regenerated in 20-30 days. To be effective botulinum toxin used alone requires the muscle to be fully paralyzed for at least a month, followed by 2-3 months of recovery, during which time the patient is usually unable to effectively use the treated eye or limb. Further, the method has been shown to have an effect lasting over 2 years, whereas the effect of botulinum toxin often requires re-injection at frequent intervals.

Further advantages of one or more aspects will become apparent from a consideration of the ensuing description and claims.

SUMMARY

According to one aspect, the fibers of a muscle are damaged by exposure to an adequate concentration and volume of a local anesthetic drug such as bupivacaine. The damaged muscle fibers are removed by the body's macrophage cells and are replaced within the residual muscle framework by new fibers regenerated by the body's satellite cells. By stretching and thereby lengthening or by relaxing and thereby shortening the residual muscle framework during this time of regeneration, the length of the resulting regenerated muscle is accordingly longer or shorter. In one embodiment, the shortening of the treated muscle improved the position and the movement of the eye to which it was attached.

DESCRIPTION

These discoveries can be beneficially applied to patients who have a structure such as an eye or a limb whose movement function is substandard because an attached muscle is too short or too long. One example is the eye muscles of person with strabismus. Here, a muscle longer or shorter than it should be will cause the eye to deviate. For example, as noted in esotropia, if the lateral (outside) rectus muscle is too long, or the medial rectus (inside) muscle is too short, the eye will turn inward. To correct this condition, known as esotropia, strabismus, or cross-eye, it would be desirable to shorten the lateral rectus muscle or to lengthen the medial rectus muscle. Surgery is the standard method of doing that. In the shortening surgery for esotropia, the lateral rectus muscles is accessed through an incision in the conjunctival layer covering of the eye, excising a segment near the end of the muscle, say, 6 mm, suturing the free end of the muscle back onto the eye, and suturing the incision in the conjunctival layer. These surgeries have disadvantages in that they are invasive, painful, carry some risk, and usually require expensive hospitalization. Such surgery must be repeated in many cases; then the scarring from the prior operation makes the surgery more difficult and less certain of outcome.

Applicant has found that purposeful exposure of an eye muscle to a local anesthetic drug in an amount sufficient to cause myotoxicity (damage to the muscle fibers), combined with relaxing the antagonist muscle during the period of regeneration, will cause such a muscle to regenerate to a shorter length. In one case of esotropia (the eye turned inward toward the nose), applicant injected the lateral rectus muscle (which pulls the eye outward) with bupivacaine. The resultant myotoxicity and weakness of the lateral rectus muscle was very pronounced. This weakness allowed the antagonist medial rectus muscle (which pulls the eye inward toward the nose) to exert its force unopposed and to rotate the eye farther inward. The lateral rectus muscle framework was thus stretched and lengthened during the period of regeneration, resulting in a longer muscle. Even though the injected lateral rectus muscle was also enlarged by exposure to bupivacaine, its increased length prevented it from pulling the eye into alignment. This same lateral rectus muscle was injected with bupivacaine a second time. Then, the antagonist medial rectus was disabled by paralyzing it with botulinum toxin. By removing the medial rectus force stretching the lateral rectus muscle framework, the latter was allowed to shorten during the period of regeneration. This resulted in regeneration of the lateral rectus muscle to a shorter length, thereby pulling the eye to a new and better position. We have repeated this treatment when the result was only partial, and achieved additional increments of muscle shortening.

We have thus demonstrated that a muscle damaged by bupivacaine myotoxicity regenerates to the length at which the remaining muscle framework is held during that regeneration. One can therefore create a longer muscle or a shorter one according to the posture of the eye as it is shortens or lengthens the attached muscle during regeneration.

A similar argument will apply to other muscles such as limb muscles, with the posture of the limb altered by bracing to stretch and lengthen or to relax and shorten the muscle framework during the period of regeneration of the fibers. Stretched facial muscles can be treated by injecting bupivacaine into the selected stretched muscle, disabling the antagonist muscles with botulinum toxin, and supporting the facial structure to shorten the framework of the selected muscle during regeneration of its muscle fibers, resulting in a shorter muscle with improved appearance and function.

Below are descriptions of several exemplary embodiments or examples of how a muscle may be exposed to an anesthetic drug to change its length.

Example 1

Esotropia Correction by Shortening of the Lateral Rectus Muscle

To improve alignment of an eye that is esotropic (turned inward or crossed), the physician will want to shorten the lateral rectus muscle, which acts to pull the eye outward. The surface of the eye is anesthetized with eye drops. A syringe is filled with 1.0 to 5.0 cc of bupivacaine, enough to fill the muscle and reach all the muscle fibers. The concentration of the bupivacaine solution is from 0.3% to 3.0%. The volume and concentration are varied depending on the amount of strengthening effect required. The syringe is attached to an injection needle whose shaft is electrically insulated. Therefore, the muscle electrical activity is picked up only by the exposed tip of the needle. The needle is attached to a wire leading to an electromyographic (EMG) recorder. A second wire leads to a ground attached to the skin of the patient's body. The tip of the needle is brought close to the muscle area, whereupon the electrical activity of the muscle is picked up and amplified by the EMG recorder as sound. The sound gets louder as the needle tip gets closer to and finally within the muscle.

The needle is then directed behind the eye towards the origin of the muscle, about 3.0 cm posterior to its point of attachment to the eye, keeping the needle within the muscle, guided by the amplitude of the recorded sound. This is important, as the drug will anesthetize the nerves and the muscle with injection of the first few drops, thereby removing the electro-audio guide to position of the needle.

The drug solution is then injected into the lateral rectus muscle starting at this deepest point, with continued injection of solution as the needle is withdrawn. In order to get the maximum effect, all the fibers of the muscle should be exposed to or perfused with the bupivacaine.

Inflammatory cells of the body (macrophages) remove the damaged muscle fiber tissue over the next few days. The damaged muscle fiber tissue releases growth factors that stimulate nearby satellite cells to multiply and to regenerate and replace the damaged muscle over the next 7-16 days.

Botulinum toxin in a dose sufficient to last 30 days is injected into the antagonist medial rectus muscle at the same time as the bupivacaine is injected into the lateral rectus muscle. This paralyzes the medial rectus muscle, preventing it from rotating the eye inward and stretching the framework of the treated lateral rectus. With this tension on the lateral rectus muscle removed, the lateral rectus muscle framework shortens several millimeters. The satellite cells regenerate muscle fibers to fit this shortened muscle framework over the period of muscle fiber regeneration, about 30 days. This has allowed successful correction of strabismus in cases where bupivacaine alone was ineffective in changing eye alignment, even though the bupivacaine had enlarged and strengthened the lateral rectus muscle.

Example 2

Esotropia Correction by Lengthening of the Medial Rectus Muscle

Suppose that the physician wants to lengthen the medial rectus muscle. Local anesthetic is injected into the medial rectus muscle to damage the muscle fibers, as described in Example 1. At the same time, botulinum toxin is injected into the medial rectus muscle, paralyzing it for a period of 30 days. During that period the antagonist lateral rectus muscle, now unopposed, stretches the framework of the medial rectus muscle. The satellite cells regenerate the muscle fibers to fit this stretched framework, resulting in a medial rectus muscle of longer length than before.

Example 3

Correction of Vertical Misalignment by Shortening of the Superior Rectus Muscle

Suppose that the physician wants to shorten the superior rectus muscle to pull the eye upward into improved alignment. Local anesthetic is injected into the superior rectus muscle to damage the muscle fibers, as described in Example 1. At the same time, botulinum toxin is injected into the antagonist inferior rectus muscle, paralyzing it for a period of 30 days, thereby removing stretch on superior rectus and allowing it to shorten. The satellite cells regenerate the superior rectus muscle fibers to fit this shortened framework, resulting in a shorter superior rectus muscle than before.

Example 4

Esotropia Correction by Lengthening of the Medial Rectus Muscle and Shortening the Lateral Rectus Muscle Suppose that an eye is very greatly deviated inward (esotropia). Local anesthetic is injected into both the lateral and medial rectus muscles to damage the muscle fibers. The injection procedure and quantity of anesthetic are as described in Example 1. The eye is held outward by placing sutures into the eye tissues and attaching them to tissues on the outer (lateral) side of the orbit. This is tolerated because the muscles, paralyzed by bupivacaine myotoxicity, do not pull against the suture to cause pain, as happens with sutures that are pulled on by active muscles. This eye position stretches the framework of the medial rectus muscle and relaxes and shortens the lateral rectus muscle. After 30 days, the muscles are regenerated, the medial rectus becomes longer and the lateral rectus becomes shorter, with resulting improvement in eye deviation.

Example 5

Correction of Flexion Contracture of the Arm

Suppose that the physician wants to lengthen a contracted flexor muscle and shorten the stretched extensor muscle in order to straighten the arm of a patient after a stroke. Local anesthetic in an adequate concentration and volume to perfuse all muscle fibers is injected into both the flexor and extensor muscles to damage the muscle fibers. Since there can be systemic toxicity from bupivacaine, several injections over several days may be needed to reach the required dose. When the target muscles are fully injected with bupivacaine, the arm is moved and braced towards extension during the period of muscle regeneration, about 30 days. This bracing will stretch the flexor muscle and relax the extensor muscle, resulting in a longer flexor muscle framework and a shorter extensor muscle framework during the period or regeneration. The satellite cells of the body will regenerate the damaged muscle fibers to fill the framework of each muscle, resulting in a longer flexor muscle and a shorter extensor muscle, resulting in improved arm position and function.

Example 6

Correction of Ptosis (Droopy Upper Eyelid)

Suppose that the physician wants to treat a droopy upper eyelid (ptosis) by shortening the levator palpebrae muscle that lifts the eyelid. Fibers of the levator muscle are exposed to the local anesthetic drug, bupivacaine, in a concentration of 0.3% to 3.0%, and in a volume of 1.0 ml to 5.0 ml by injection into the levator muscle using EMG localization, as described in Example 1. At the same time, the orbicularis muscle that closes the eyelid, the antagonist of the levator, is disabled with botulinum for a period of 30 days, thereby removing tension on the levator muscle and allowing the levator muscle framework to shorten during the period of regeneration, resulting in a shorter muscle that raises the eyelid into an improved position.

Example 7

Correction of Eyelid Retraction

Suppose that the levator muscle lifting the upper eyelid is too short and lifts the upper eyelid too much, exposing the cornea and creating irritation or cosmetic deformity. To lengthen it so that it will better cover the cornea and close the eye, fibers of the levator muscle are exposed to the local anesthetic drug, bupivacaine, in a concentration of 0.3% to 3.0%, and in a volume of 1.0 ml to 5.0 ml by injection into the levator muscle. The upper eyelid is forcibly pushed downward or is sutured in a downward position for 30 days to stretch the levator during the period of regeneration of the levator muscle fibers. The regenerating muscle fibers will fill the lengthened muscle framework, making a longer levator muscle, resulting in less retraction and improved eyelid position.

Both amino-ester and amino amide local anesthetics have the property of causing muscle damage, but those of the amino-amide class are more powerful in this regard and are preferred; bupivacaine, ropivacaine, and etidocaine are examples of drugs of this class.

The use of an EMG to guide drug placement is not a requirement of this method. Ultrasound, magnetic resonance imaging, and radiographic techniques are among the alternative methods for use in localizing drug placement into muscles. Where the muscle can be directly seen, as in the limb, visual guidance is adequate.

CONCLUSIONS, RAMIFICATIONS, AND SCOPE

I have thus described a method, many aspects of which can lengthen or shorten and thereby improve the manner of treatment of conditions in which muscle function is inadequate. The eye muscle condition of strabismus ("crossed eyes") can be treated both by substitution of this simpler method for surgery, and by application of the method in cases where surgery on the eye muscles is inappropriate. The method for changing muscle lengths has advantages over surgical treatment in that simple injections in the office suffice, with no need for expensive hospitalization and extended recovery. The material injected is an anesthetic, so that pain is minimal, and there is no pain following injection. The method has advantages over botulinum toxin injection used alone in that the injected muscle will recover its former action within 7-16 days and then go on to improved function within 20-30 days. To get a lasting effect from botulinum toxin the muscle must be paralyzed for over 30 days, with additional weakness for 2-3 months before full recovery. During that time the patient is usually unable to use the paralyzed eye effectively. The method has been shown to have an effect lasting up to two years, whereas botulinum toxin often requires re-injection at frequent intervals.

While the above description contains many specificities, these should not be construed as limitations on the scope, but as exemplifications of some presently preferred embodiments. Many other ramifications and variations are possible within the teachings. For example, while the method had been discussed with reference to the eye muscles, eyelid muscle, facial muscles and arm muscles, striated muscles with inappropriate length in all parts of the body can be treated by this method. While bupivacaine is the drug most used because of it availability and demonstrated toxicity to muscles, other local anesthetic drugs, especially of the amino-amide class, such as ropivacaine and etidocaine may show equal or greater ability to stimulate change in muscle length. Plasmocid and related compounds have an action on the Z line of muscle fibers similar to that of bupivacaine and may be employed to lengthen or shorten muscles by this method. Beyond human use, application to domestic animals of all types is envisioned, both as treatment and to enhance function or appearance. Thus the scope should be determined by the appended claims and their legal equivalents, and not by the examples given.

I claim:

1. A method of using a local anesthetic drug to aid in lengthening or shortening a skeletal muscle to improve its function, comprising:
exposing the fibers of such muscle to a concentration of said local anesthetic drug in sufficient quantity to selectively damage the fibers of such muscle leaving the muscle framework intact;
holding said muscle framework at the desired longer or shorter length while the fibers of such muscle are regenerated to fill that framework, thereby resulting in a regenerated muscle of longer or shorter length than originally present.

2. The method of claim 1 wherein such muscle is an eye muscle, and said local anesthetic drug is bupivacaine in a concentration of 0.3% to 3.0%, and in a volume of 1.0 ml to 5.0 ml, given by injection into such selected eye muscle, and the eye is then held with sutures in a position to shorten the framework of the selected muscle during muscle fiber regeneration, so that the regenerated muscle is shorter and therefore pulls the eye into a position of improved alignment.

3. The method of claim 1 wherein such muscle is an eye muscle, and said local anesthetic drug is bupivacaine in a concentration of 0.3% to 3.0%, and in a volume of 1.0 ml to 5.0 ml given by injection into such eye muscle, and the eye is then held with sutures to stretch and lengthen framework of the injected muscle during regeneration, so that the regenerated muscle is longer than before, thereby allowing the eye to move into a position of improved alignment.

4. The method of claim 1 wherein such muscles are a pair of reciprocally acting eye muscles, and said local anesthetic drug is bupivacaine in a concentration of 0.3% to 3.0%, and in a volume of 1.0 ml to 5.0 ml given by injection into both such eye muscles, and the eye is then held with sutures in a position shortening one muscle and stretching and lengthening the other muscle during regeneration, with the purpose of creating shorter and longer muscles, respectively, that pull the eye into improved alignment.

5. The method of claim 1 wherein such muscle is an eye muscle, and said local anesthetic drug is bupivacaine in a concentration of 0.3% to 3.0% and in a volume of 1.0 ml to 5.0 ml given by injection into such selected eye muscle, and the antagonist muscle is injected with botulinum toxin to paralyze it, thereby removing tension on the selected muscle and its framework, allowing them to shorten for the period of regeneration, with the purpose of shortening the selected muscle so that it pulls the eye into improved alignment.

6. The method of claim 1 wherein such muscle is an eye muscle, and said local anesthetic drug is bupivacaine in a concentration of 0.3% to 3.0% and in a volume of 1.0 ml to 5.0 ml given by injection into such selected eye muscle, and the selected muscle is injected also with botulinum toxin to paralyze the selected muscle for the period of regeneration so that the antagonist can stretch and lengthen the selected muscle and its framework during regeneration, with the purpose of lengthening the muscle so that it allows improved alignment.

7. The method of claim 1 wherein muscle fibers of the levator muscle of the eyelid are exposed to a local anesthetic drug such as bupivacaine in a concentration of 0.3% to 3.0%, and in a volume of 1.0 ml to 5.0 ml, given by injection into the levator muscle, and the antagonist of the levator, the orbicularis muscle that closes the eye, is injected with botulinum toxin to paralyze it, thereby removing tension on the levator muscle and allowing the levator muscle and its framework to shorten over the period of regeneration, with the purpose of shortening the levator palpebrae muscle and thereby raising the eyelid into an improved position.

8. The method of claim 1 wherein such muscle fibers are selected from the levator palpebrae muscle of the eyelid and exposed to the local anesthetic drug, bupivacaine, in a concentration of 0.3% to 3.0%, and in a volume of 1.0 ml to 5.0 ml by injection into the muscle, and at the same time, botulinum toxin in a dose appropriate to last 20-30 days, is injected into the levator, paralyzing it so that the antagonist orbicularis muscle can stretch the levator during the period of regeneration of the levator muscle fibers so that the regenerated muscle fibers will fill the stretched muscle framework, making a longer levator muscle that can better cover the cornea and front of the eye.

9. The method of claim 1 wherein such muscle fibers are selected from the levator palpebrae muscle of the eyelid and exposed to the local anesthetic drug, bupivacaine, in a concentration of 0.3% to 3.0%, and in a volume of 1.0 ml to 5.0 ml by injection into the muscle, and at the same time, the eyelid is sutured closed or is forcibly held closed by a pressure bandage for a period of 20-30 days, thereby stretching the levator during the period of regeneration of the levator muscle fibers so that the regenerated muscle fibers will fill the stretched muscle framework, making a longer levator muscle that can better cover the cornea and front of the eye.

10. A method of lengthening or shortening a skeletal muscle comprising:
identifying and selecting muscle fibers of skeletal muscle of a patient that is relatively shorter or longer than the optimum operating length;
exposing the fibers of such a muscle to a concentration of a local anesthetic drug in sufficient quantity to damage the fibers from the myotoxicity of the drug;
holding the muscle at a longer or shorter length during the period of muscle regeneration so that the muscle satellite cells regenerate the muscle to a longer or shorter length, thereby allowing the muscle to give improved position and function.

11. The method of claim 10 wherein such muscle is a stretched or lengthened extensor muscle of the finger, and said local anesthetic drug is bupivacaine in a concentration of 0.3% to 3.0%, and in a volume of 1.0 ml to 20.0 ml, given by injection into said muscle at one time or over several sessions, depending on the required dose and the need to avoid a cardiotoxic concentration at any time, and the finger is then held with a brace in a position to relax and thereby shorten the muscle framework during muscle fiber regeneration, so that the satellite cells regenerate the muscle to a shorter length, so that the muscle pulls the finger into an improved position and function.

12. The method of claim 10 wherein such muscle is a tight or shortened extensor muscle of the finger, and said local anesthetic drug is bupivacaine in a concentration of 0.3% to 3.0%, and in a volume of 1.0 ml to 20.0 ml, given by injection into said muscle at one time or over several sessions, depending on the required dose and the need to avoid a cardiotoxic concentration at any time, and the finger is then held with a brace in a position to stretch the muscle framework during muscle fiber regeneration, so that the satellite cells regenerate the muscle to a longer length, and therefore the muscle allows the finger to assume an improved position and function.

13. The method of claim 10 wherein such muscles are a pair of reciprocally acting finger muscles, and said local anesthetic drug is bupivacaine in a concentration of 0.3% to 3.0%, and in a volume of 1.0 ml to 20.0 ml given by injection into each of such muscles, at one time or over several sessions, depending on the required dose and the need to avoid a cardiotoxic concentration at any time, and the finger is then held with bracing in a position shortening one muscle and stretching and lengthening the other muscle during regeneration, with the purpose of creating shorter and longer muscles, respectively, that pull the finger into an improved position and function.

14. The method of claim 10 wherein such muscle is a finger muscle, and said local anesthetic drug is bupivacaine in a concentration of 0.3% to 3.0% and in a volume of 1.0 ml to 20.0 ml given by injection into such finger muscle, and the antagonist muscle is disabled by injection of botulinum toxin or a similar drug, thus removing tension on the selected finger muscle and allowing its framework to shorten during the period of regeneration, with the purpose of shortening such selected muscle so that it pulls the finger into improved position and function.

15. The method of claim 10 wherein such muscle is the frontalis muscle that lifts the brow, that has become stretched, and said local anesthetic drug is bupivacaine in a concentration of 0.3% to 3.0% and in a volume of 1.0 ml to 20.0 ml given by injection into the frontalis muscle, at one time or over several sessions, depending on the required dose and the need to avoid a cardiotoxic concentration at any time, and the antagonist muscles are injected with botulinum toxin or a similar drug to weaken them for the period of regeneration, so that the brow can be elevated with tape or bandages to shorten the framework of the frontalis muscle during regeneration, with the purpose of shortening the frontalis muscle so that it provides improved position and function.

16. The method of claim 10 wherein the identified muscles in an arm with flexion contracture are the shortened biceps flexor muscle, and the stretched triceps extensor muscle, and said local anesthetic drug is bupivacaine in a concentration of 0.3% to 3.0% and in a volume of 1.0 ml to 20.0 ml given by injection into the identified muscles, at one time or over several sessions, depending on the required dose and the need to avoid a cardiotoxic concentration at any time, and the arm is then braced to lengthen the biceps muscle and its framework and to shorten the triceps muscle and its framework for the period of regeneration, so that the muscles will regenerate longer and shorter, respectively, with the purpose of providing improved position and function to the arm.

* * * * *